US012576209B1

(12) United States Patent
    Delgado

(10) Patent No.: US 12,576,209 B1
(45) Date of Patent: Mar. 17, 2026

(54) HOUSING FOR HYPODERMIC DEVICE

(71) Applicant: Jorge Delgado, Homestead, FL (US)

(72) Inventor: Jorge Delgado, Homestead, FL (US)

( * ) Notice: Subject to any disclaimer, the term of this patent is extended or adjusted under 35 U.S.C. 154(b) by 726 days.

(21) Appl. No.: 18/057,078

(22) Filed: Nov. 18, 2022

(51) Int. Cl.
    A61M 5/20          (2006.01)
    A61M 5/32          (2006.01)

(52) U.S. Cl.
    CPC ............ A61M 5/20 (2013.01); A61M 5/3202 (2013.01); A61M 2005/2073 (2013.01)

(58) Field of Classification Search
    CPC ................ A61M 5/20; A61M 5/3202; A61M 2005/2073
    See application file for complete search history.

(56) References Cited

U.S. PATENT DOCUMENTS

| | | | |
|---|---|---|---|
| 5,161,681 A | * | 11/1992 | Kemp .................. A61M 5/3205 |
| | | | 206/364 |
| 5,950,827 A | | 9/1999 | Odom et al. |
| 6,405,912 B2 | | 6/2002 | Giannou |
| 6,595,362 B2 | | 7/2003 | Penney et al. |
| 7,635,348 B2 | | 12/2009 | Raven et al. |
| 9,272,475 B2 | | 3/2016 | Ranade et al. |
| 9,381,294 B2 | | 7/2016 | Ziegner |
| 9,827,168 B2 | | 11/2017 | Honarvar et al. |
| 10,441,714 B2 | | 10/2019 | Kapas et al. |
| 10,722,427 B2 | | 7/2020 | Cantor |
| 11,143,448 B2 | | 10/2021 | Tsuno |
| 11,344,473 B2 | | 5/2022 | Weikart et al. |
| 2005/0148933 A1 | * | 7/2005 | Raven .................. A61M 5/3202 |
| | | | 604/111 |
| 2010/0282762 A1 | * | 11/2010 | Leonard ............. B65D 81/3841 |
| | | | 220/592.2 |
| 2019/0145688 A1 | * | 5/2019 | Tsuno .................... B65D 81/20 |
| | | | 62/129 |
| 2019/0162460 A1 | | 5/2019 | Minkyu |

* cited by examiner

*Primary Examiner* — Tasnim Mehjabin Ahmed
(74) *Attorney, Agent, or Firm* — ALBERT BORDAS, P.A.

(57) ABSTRACT

A housing for hypodermic device including a housing assembly, a hypodermic device housed therein, twist off top and bottom caps. The housing assembly includes an upper and lower ends, exterior and interior walls. The exterior and interior walls definine a vacuum sealed in-between space, and the interior wall defines an interior cavity. The top and bottom caps include first and second tabs, respectively. The hypodermic device has proximal and distal ends. The hypodermic device includes auto injectors such as epinephrine auto injector, insulin auto injector or similar. The exterior and interior walls are vacuum sealed layers made of a rigid material that protect the hypodermic device from impact and accidental activation and keep the hypodermic device at a range of temperature for a longer period of time. A ring attachment is adjacent to the upper end, and it secures to backpacks, purses, garments or similar.

14 Claims, 3 Drawing Sheets

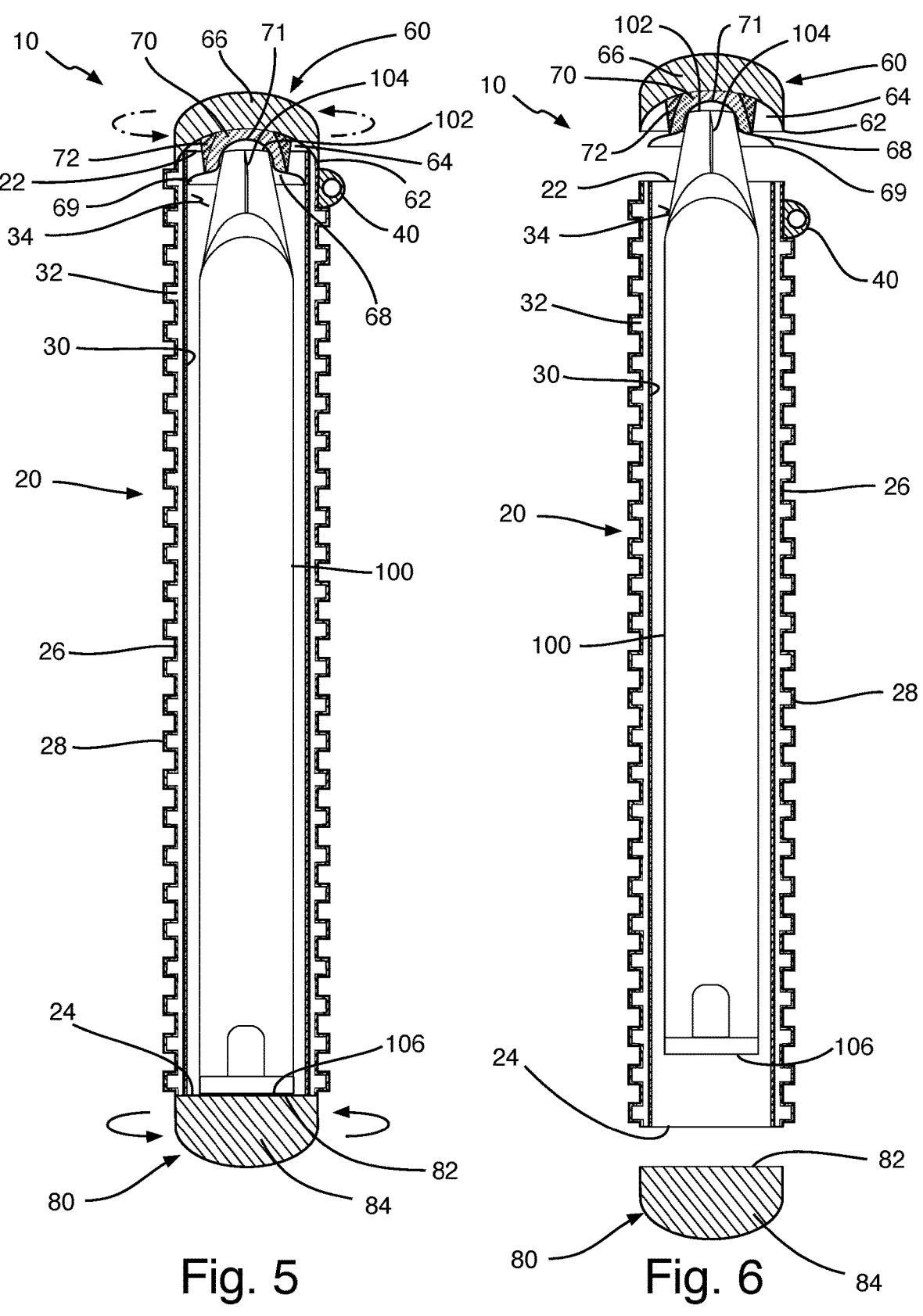
Fig. 5                    Fig. 6

HOUSING FOR HYPODERMIC DEVICE

BACKGROUND OF THE INVENTION

1. Field of the Invention

The present invention relates to housings, and more particularly, to housings for hypodermic devices including epinephrine auto injectors, insulin auto injectors, and devices having syringes for similar purposes.

2. Description of the Related Art

Epinephrine injection is used for emergency treatment of severe allergic reactions (including anaphylaxis) to insect bites or stings, medicines, foods, and other substances. It is also used to treat anaphylaxis caused by unknown substances or triggered by exercise. An epinephrine autoinjector (or adrenaline autoinjector, also known by the trademark "EpiPen", is a medical device for injecting a measured dose or doses of epinephrine by means of autoinjector technology. Specifically, Epinephrine autoinjectors are hand-held devices carried by those who have severe allergies (anaphylaxis) the epinephrine delivered by the device is an emergency treatment.

When an allergic emergency (anaphylaxis) is suspected, epinephrine solution should be given as soon as possible as an intramuscular injection. That is why patients with anaphylaxis need to carry an Epinephrine injection with them all the time. However, Epinephrine injection, USP labeling instructs it should be stored in the carrier tube provided at a temperature of approximately 20-25° C. (68-77° F.), preferably. Epinephrine is temperature sensitive.

Other hypodermic devices such as insulin auto injector or any other device for the same purpose are required to maintain the medication within a required range of temperature, particularly for patients carrying autoinjectors and during storage in emergency vehicles.

Applicant believes that one of the closest references corresponds to U.S. Pat. No. 5,950,827 A issued to Odom, et al. on Sep. 14, 1999, for an injector pen storage case. However, it differs from the present invention because Odom, et al. teaches an injector pen storage case for storing an injector pen, such as used by highly allergic individuals to inject epinephrine, that includes a mechanism for indicating when an injector pen housed within the storage case has leaked and is no longer usable.

Applicant believes that another reference corresponds to U.S. Pat. No. 11,143,448 B2 issued to Tsuno on Oct. 12, 2021, for a transport device. However, it differs from the present invention because Tsuno teaches a transport device, which can perform easily thermal storage temperature controlling treatment of the thermal storage material even at a cell transport destination. The transport device of the present invention includes: a thermally insulated container that has a cylindrical shape and a bottom, a thermal storage material disposed along the inner circumferential surface of the thermally insulated container, and a temperature control unit that is detachably fitted on the thermally insulated container and is for performing thermal storage temperature controlling treatment on the thermal storage material, wherein the temperature controlling unit comprises a heat transferring body for performing the thermal storage temperature control processing on the thermal storage material when the unit is fitted on the thermally insulated container, and a storage space formed inside the heat-transferring body for storing a stored object so that the object can be freely put in and taken out.

Applicant believes that another reference corresponds to U.S. Pat. No. 9,381,294 B2 issued to Ziegner on Jul. 5, 2016, for an auto-injector case. However, it differs from the present invention because Ziegner teaches an insulated, epinephrine auto-injector case that also includes a rapid-opening cap, two spring-loaded chambers, each with a rapid-opening cap to facilitate immediate and easy availability of the auto-injector for grasping by the user.

Applicant believes that another reference corresponds to U.S. Pat. No. 9,827,168 B2 issued to Honarvar, et al. on Nov. 28, 2017, for a beverage container system. However, it differs from the present invention because Honarvar, et al. teaches a beverage container system for babies through small children has a thermally insulated outer container, which is sized to receive a standard baby bottle and hold it therein with a retainer securable to hold a standard baby bottle. A cap may be positioned over the baby bottle nipple system to protect the nipple. The retainer and standard baby bottle may be removed. An adapter may be thereupon attached to the outer container which can be used with other beverage accessories such as a sippy cup, straw spout and drink tube spout.

Applicant believes that another reference corresponds to U.S. Pat. No. 11,344,473 B2 issued to Weikart, et al. on May 31, 2022, for a coated packaging. However, it differs from the present invention because Weikart, et al. teaches a vessel has an interior surface facing a lumen. The interior surface includes a tie coating or layer, a barrier coating or layer, and a pH protective coating or layer. The tie coating or layer can comprise SiOxCy or SiNxCy, where x is from about 0.5 to about 2.4 and y is from about 0.6 to about 3. The barrier coating or layer can comprise SiOx, wherein x is from 1.5 to 2.9. The barrier coating or layer reduces the ingress of atmospheric gas into the lumen. The pH protective coating or layer can comprise SiOxCy or SiNxCy, as well. In an embodiment, in the presence of a fluid composition contained in the lumen and having a pH between 5 and 9, the calculated shelf life of the package can be more than six months at a storage temperature of 4 degree C.

Applicant believes that another reference corresponds to U.S. Pat. No. 9,272,475 B2 issued to Ranade, et al. on Mar. 1, 2016, for a thermally insulated VIP sandwich shipper and method of making same. However, it differs from the present invention because Ranade, et al. teaches a thermally insulated VIP sandwich shipper for a temperature sensitive payload is provided. The shipper comprises an outer shell, an inner shell and vacuum insulated panels sandwiched therebetween. The outer shell and the inner shell may be unitary rigid structures made of an expanded foam material and comprising a bottom having a perimeter and sides extending from the bottom perimeter and terminating in a rim. The inner shell rim may be spaced from the outer shell rim to define a gap, the gap being sealed to create an enclosed space within which the vacuum insulated panels are located. Each vacuum insulated panel may be oriented substantially orthogonally to at least one adjacent vacuum insulated panel and have an edge that abuts the adjacent vacuum insulated panels.

Applicant believes that another reference corresponds to U.S. Pat. No. 6,405,912 B2 issued to Giannou on Jun. 18, 2002, for a protective case for carrying a fragile object. However, it differs from the present invention because Giannou teaches a protective case to be worn by an individual for carrying a medical device that may be required in case of allergic or asthmatic reactions or diabetic reactions. The case includes a rigid receptacle to protect the medical device. The case can be worn on a person's belt, or it may be permanently fixed to a belt or a band that can be worn around the waist, an arm or a leg. For a standard syringe, the receptacle comprises an elongated, rigid cylindrical tube which fits closely about the syringe. The receptacle further includes an open end that is covered by a cap that can be readily removed to provide easy access to the syringe inside the tube and which protects the syringe from contamination. The case is unobtrusive in appearance and does not hamper the individual's movements thus allowance it to be worn at all times.

Applicant believes that another reference corresponds to U.S. Pat. No. 10,441,714 B2 issued to Kapas, et al. on Oct. 15, 2019, for a protective case for an auto-injector. However, it differs from the present invention because Kapas, et al. teaches a protective case for an auto-injector. The medicament contained within these auto-injectors can be susceptible to degradation due to exposure to extreme temperatures and light. Thus, one embodiment of the protective case reduces the rate of heat transfer between the internal storage compartment of the case and the external atmosphere by including particularly configured vacuum chambers. Additionally, as auto-injectors become smaller, portability can be desirable. Thus, another embodiment of the protective case includes low-profile cases that allow the user to keep the auto-injector with them, e.g., by attaching the case to a common everyday item.

Applicant believes that another reference corresponds to U.S. Pat. No. 7,635,348 B2 issued to Raven, et al. on Dec. 22, 2009, for a container for medicament automatic injector and automatic injector adapted therefor. However, it differs from the present invention because Raven, et al. teaches containers for automatic injectors and automatic injectors adapted for those containers. The containers include structures adapted to retain and, optionally, cripple the needle of the automatic injector when the automatic injector is inserted into the container after use. Depending on the embodiment, an indicator may be included, either as part of the container or as part of the automatic injector, to indicate whether or not the automatic injector has been used. If the indicator is provided as a part of the automatic injector, a corresponding portion of the container may be formed of a light permeable material. The container may also include features, such as an eyelet over the closed end, designed to cushion the automatic injector. Cushioning and shock absorbing features may also be provided inside the container. A clip is also disclosed. The clip is designed to attach two or more containers together.

Applicant believes that another reference corresponds to U.S. Pat. No. 6,595,362 B2 issued to Penney, et al. on Jul. 22, 2003, for cases for medication delivery devices. However, it differs from the present invention because Penney, et al. teaches cases for carrying medication delivery devices such as auto-injectors, syringes or vials. The cases include a cradling structure to protect the medication delivery device from jostling and impact encountered during transport.

Applicant believes that another reference corresponds to U.S. Pat. No. 10,722,427 B2 issued to Cantor on Jul. 28, 2020, for a hermetically sealable case for medical device and medicine. However, it differs from the present invention because Cantor teaches a case including a pocket for hermitically storing medical device(s) and medicine. The case may include a manual or motorized pump that can generate vacuum pressure within the pocket to thermally insulate the pocket from the atmosphere to minimize temperature fluctuations within the pocket.

The case may also include a cooling and/or heating system to control the temperature within the pocket within a desired range to prolonging the potency and the life expectancy of the drug, such as epinephrine, stored within the pocket. The case may also be equipped with a communication device that can link with user's mobile device so that in case of an emergency, the communication device can alert the mobile device, which can then notify emergency personal for assistance.

Applicant believes that another reference corresponds to U.S. Patent Application Publication No. US20190145688 A1, published on May 16, 2019, to Katsuhiro Tsuno for a transport container. However, it differs from the present invention because Katsuhiro Tsuno teaches a transport container comprising; a first container having a first inner wall with a storage space for storing a transported object and a first outer wall provided on the outside of the first inner wall so as to form, with the first inner wall, a vacuum space therebetween; a first lid that is heat-insulating and is for removably sealing a first opening of the first container; a second container having a second inner wall with a space for storing the first container and the first lid and a second outer wall provided on the outside of the second inner wall so as to form, with the second inner wall, a vacuum space therebetween; a second lid that is heat-insulating and is for removably sealing a second opening of the second container; and a heat storage material for surrounding the transported object inside the storage space.

Applicant believes that another reference corresponds to U.S. Patent Application Publication No. US20100282762 A1, published on Nov. 11, 2010, to Larry Wendall Leonard for a Mobile Insulin Storage Cooler. However, it differs from the present invention because Larry Wendall Leonar teaches a bottle for cooling or warming a bottle of insulin having a first bottle of an insulating material for receiving a liquid or solid cooling or warming medium having at its top end male threads for receiving a screw on cup shaped cover and a second bottle of non-insulating material located within the first bottle. The second bottle has a size that can receive a 10 ML volume bottle of insulin that is to be kept at a temperature of between 36 degrees F. and 87 degrees F. by the cooling or warming medium in the first bottle for extending the storage life of insulin in the bottle which is located in the second bottle.

Applicant believes that another reference corresponds to U.S. Patent Application Publication No. US20190162460 A1, published on May 30, 2019, to Minkyu for a temperature controlled container. However, it differs from the present invention because Minkyu teaches a temperature controlled container including a case, which has a storage space formed therein; a thermoelectric element; a heat transfer body in communication with the thermoelectric element and facing the storage space. The heat transfer body includes a heat transfer case which has an enclosed space formed therein and is wider than the thermoelectric element, and includes a portion facing the thermoelectric element; a phase change material which is accommodated in the enclosed space; and a heat transfer body which is disposed in the heat transfer case so as to be positioned in the enclosed space. The heat transfer body has a first body portion which is in communication with the portion of the heat transfer case facing the thermoelectric element and a second body portion, and the first body portion in communication with the second body portion.

Other patents describing the closest subject matter provide for a number of more or less complicated features that fail to solve the problem in an efficient and economical way. None of these patents suggest the novel features of the present invention.

SUMMARY OF THE INVENTION

The instant invention is a housing for hypodermic device, comprising a housing assembly with an upper end, a lower end, an exterior wall and an interior wall. The exterior wall and the interior wall define a vacuum sealed in-between space. The interior wall defines an interior cavity. A top cap comprises first connecting ends, a base and a first tab. The top cap being removably mounted to the upper end. The top cap being a twist off cap. A bottom cap comprises a second connecting end and a second tab. The bottom cap being removably mounted to the lower end, the bottom cap being a twist off cap. A hypodermic device has a proximal end and a distal end. The hypodermic device being housed inside the housing assembly, wherein the proximal end is aligned with the upper end and the distal end is aligned with the lower end. The proximal end being closed with the top cap and the distal end being closed with the bottom cap.

The top cap further comprises a hypodermic device supporting portion, a retaining member and a supporting structure, wherein the base with the first connecting ends mount upon the upper end. The first tab is fixedly mounted onto the base. The retaining member is disposed inside the supporting structure, and the supporting structure is adapted to rigidly support the retaining member. The hypodermic device supporting portion extends from the retaining member. The retaining member has a bay having) cooperative shape and dimensions to securely receive a hypodermic device supporting portion therein. The hypodermic device supporting portion has a cooperative shape and dimensions to snugly hold the proximal end of the hypodermic device. The hypodermic devise supporting portion comprises a wider portion. The wider portion extends beyond the first connecting end. The wider portion is accommodated inside the interior cavity and snugly fit onto the interior wall.

The hypodermic devices are auto injectors, epinephrine auto injectors, and insulin auto injectors. The exterior wall and the interior wall are configured as vacuum sealed layers made of a rigid material that protect the hypodermic device from impact and accidental activation. The rigid material is stainless steel or other material having similar characteristics. The exterior wall and the interior wall are configured to keep the hypodermic device at a range of suitable temperature for a predetermined period of time. Thus, protecting the hypodermic device for securely storing and transportation. The exterior wall comprises peripheral ridges. The housing assembly has a substantially elliptical cross section with cooperative dimensions to receive the hypodermic device therein. The top cap and the bottom cap are adapted to hold the hypodermic device centered inside the interior cavity. The housing assembly further comprises a ring attachment adjacent to the upper end. The ring attachment is adapted to be used to secure the housing for hypodermic device to backpacks, purses, garments carried or worn.

It is therefore one of the main objects of the present invention to provide a housing for hypodermic devices.

It is another object of this invention to provide a housing for hypodermic devices for securely store and transport auto-injectors, and protects the hypodermic devise housed therein from impact and accidental activation.

It is another object of this invention to provide a housing for hypodermic devices that regulates the internal temperature, keeping the auto-injector in a secure range of temperature for a longer period of time.

It is another object of this invention to provide a housing for hypodermic devices that comprises two vacuum sealed layers of stainless steel.

It is another object of this invention to provide a housing for hypodermic devices that comprises twist off caps on both ends.

It is another object of this invention to provide a housing for hypodermic devices that comprises a ring attachment to secure to backpacks, purses, garments or any other suitable things worn or carried by user.

It is another object of this invention to provide a housing for hypodermic devices comprising upper and lower caps, which will hold the auto injector centered in the case to allow for air space.

It is another object of this invention to provide a housing for hypodermic devices that is volumetrically efficient for carrying, transporting, and storage.

It is another object of this invention to provide a housing for hypodermic devices that can be readily disassembled without the need of any special tools.

It is another object of this invention to provide a housing for hypodermic devices, which is of a durable and reliable construction.

It is yet another object of this invention to provide such devices that are inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 5 is a cross-sectional view of the present invention taken along lines 5-5 from FIG. 2.

FIG. 6 is the cross-sectional view of FIG. 3, showing the top and bottom caps removed.

DETAILED DESCRIPTION OF THE PREFERRED EMBODIMENT

Figure 1:
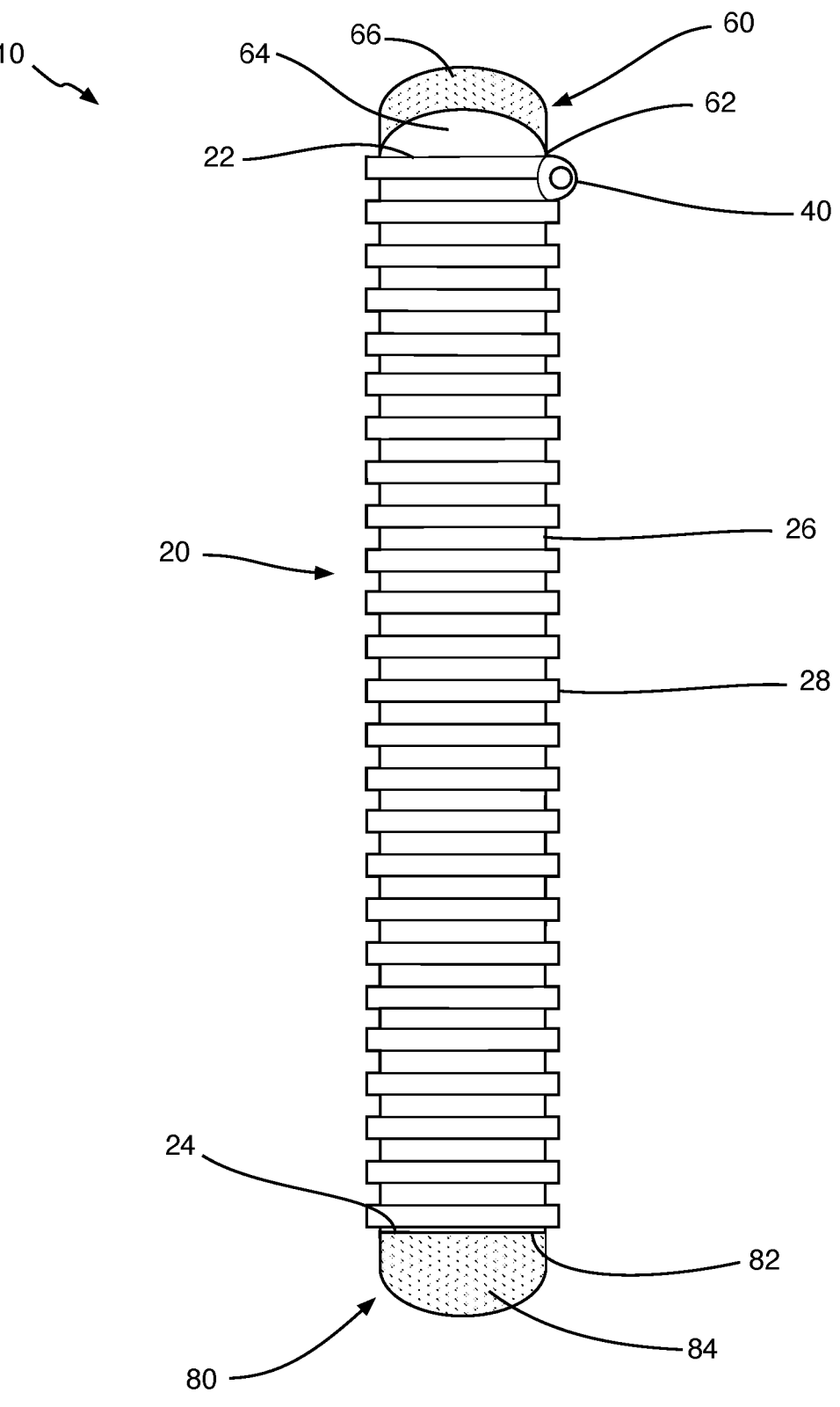
FIG. 1 is a front view of a housing for hypodermic devices.

Referring now to the drawings, the present invention is generally referred to with numeral 10. It can be observed that it basically includes housing assembly 20, top cap 60, and bottom cap 80.

Figures 2, 3, 4:
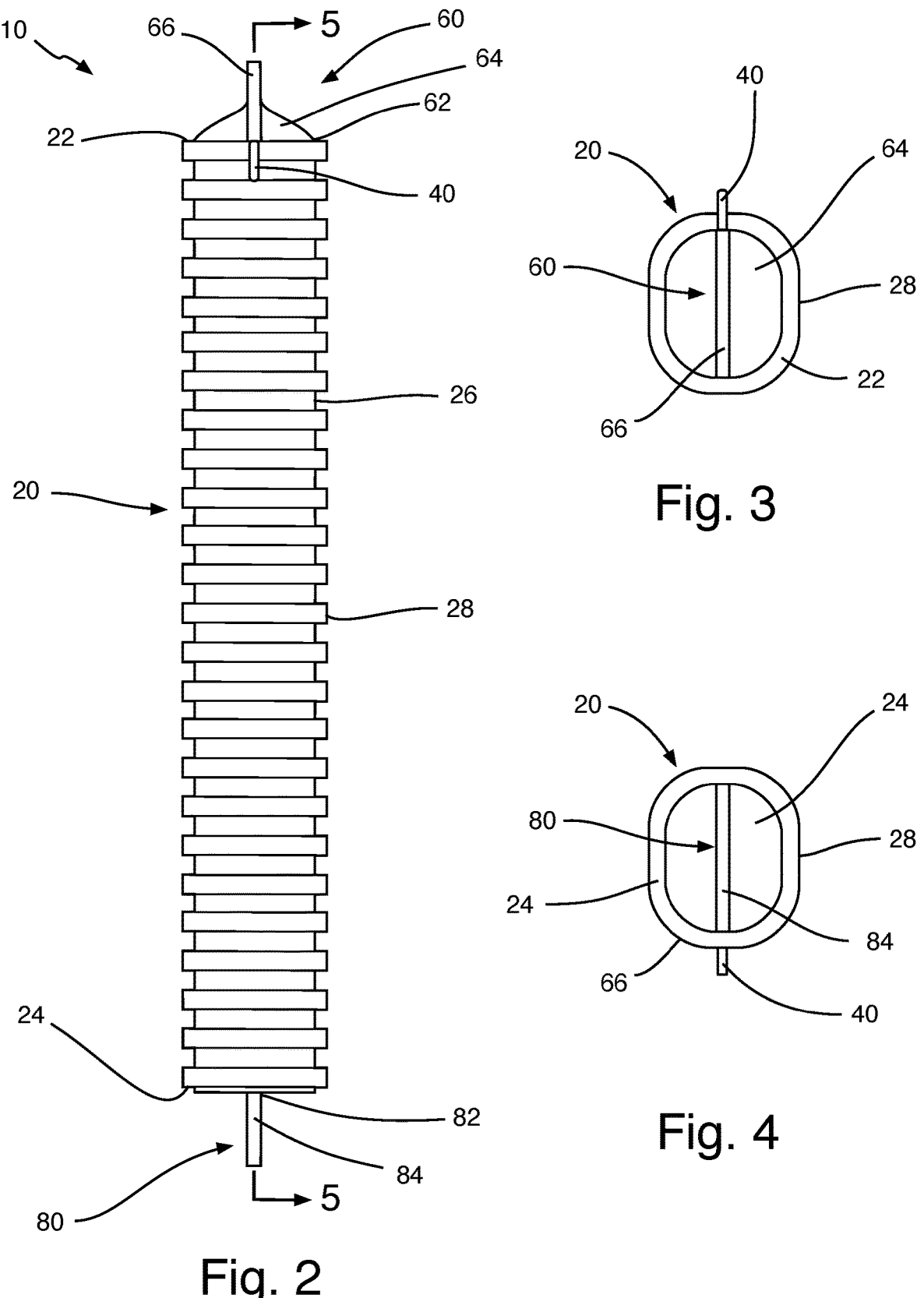
FIG. 2 is a side view of the present invention.
FIG. 3 is a top view of the present invention.
FIG. 4 is a bottom view of the present invention.

As seen in FIGS. 1 and 2, housing assembly 20 comprises upper end 22, lower end 24, and exterior wall 26. In a preferred embodiment, exterior wall 26 comprises a plurality of peripheral ridges 28 protruding therefrom. Peripheral ridges 28 are horizontally disposed, preferably. However, other embodiments could have peripheral ridges 28 vertically disposed. Peripheral ridges 28 slow heat transfer. Housing assembly 20 further comprises ring attachment 40 adjacent to upper end 22. Ring attachment 40 may be used to secure housing for hypodermic device 10 to backpacks, purses, garments, or any other suitable things carried and/or worn by a user. Top cap 60 is removably mounted at upper end 22. Top cap 60 comprises connecting ends 62, base 64 and tab 66. Bottom cap 80 is removably mounted to lower end 24. Bottom cap 80 comprises connecting end 82 and tab 84.

As seen in FIGS. 3 and 4, housing for housing assembly 20 has a substantially elliptical cross section, with coopera- tive dimensions to receive hypodermic device 100 therein as seen in FIGS. 5 and 6. Hypodermic device 100 include, but are not limited to, auto injectors such as epinephrine auto injectors, insulin auto injectors or any other devices com- prising syringes for similar purposes.

As seen in FIGS. 5 and 6, top cap 60 and bottom cap 80 are twist off caps. Top cap 60 and bottom cap 80 hold hypodermic device 100 centered inside interior cavity 34 that is defined by interior wall 30 of housing assembly 20. This allows for air space in between interior wall 30 and hypodermic device 100. Exterior wall 26 and interior wall 30 define vacuum sealed in-between space 32. In a preferred embodiment, exterior wall 26 and interior wall 30 are configured as vacuum sealed layers made of a rigid material, such as stainless steel or any other suitable material. This material and configuration, protects hypodermic device 100 from impact and accidental activation. Also, it keeps hypo- dermic device 100 housed therein, at a secure range of suitable temperature for a longer period of time. Addition- ally, its steady structure protects hypodermic device 100 for securely store and transport.

Top cap 60 further comprises hypodermic device support- ing portion 68, retaining member 70 and supporting struc- ture 72. Base 64 with connecting end 62 mount upon upper end 22. Tab 66 is fixedly mounted onto base 64. Supporting structure 72 rigidly supports retaining member 70 disposed inside the former. Hypodermic device supporting portion 68 extends from retaining member 70. Retaining member 70 has bay 71 having a cooperative shape and dimensions to securely receive hypodermic device supporting portion 68. Hypodermic device supporting portion 68 has cooperative shape and dimensions to snugly hold proximal end 102 of hypodermic device 100. Hypodermic devise supporting por- tion 68 has wider portion 69, which extends beyond con- necting end 62 to be accommodated inside interior cavity 34, as best seen in FIG. 5. Wider portion 69 snugly fits onto interior wall 30.

Hypodermic device 100 has proximal end 102, needle 104 and distal end 106. Hypodermic device 100 is housed inside interior cavity 34 wherein proximal end 102 is aligned with upper end 22, and distal end 106 is aligned with lower end 24. Top cap 60 mounts upon upper end 22 in a way that proximal end 102 is kept inside hypodermic device support- ing portion 68, while wider portion 69 keeps it spaced apart from interior wall 30. Bottom cap 80 mounts upon lower end 24.

As best seen in FIG. 6, for use, top cap 60 and bottom cap 80 are twisted off and removed. However, since proximal end 102 is snugly held by hypodermic device supporting portion 68, hypodermic device 100 is extracted from interior cavity 34. Once extracted, a user removes proximal end 102 from hypodermic device supporting portion 68 for admin- istration. The fact that proximal end 102 is snugly held by hypodermic device supporting portion 68, guarantees that hypodermic device 100 is not activated by accident, thus preventing needle 104 from projecting beyond proximal end 102.

In a preferred embodiment, housing for hypodermic device 10 helps maintain an internal temperature range of approximately 67° F. to 76° F. for epinephrine. Housing for hypodermic device 10 helps maintain a range of suitable temperatures for other medications, and for predetermined long periods of time even in warmer or cooler environments.

The foregoing description conveys the best understanding of the objectives and advantages of the present invention. Different embodiments may be made of the inventive con- cept of this invention. It is to be understood that all matter disclosed herein is to be interpreted merely as illustrative, and not in a limiting sense.

What is claimed is:

1. A housing for hypodermic device, comprising:
A) a housing assembly comprising an upper end, a lower end,
an exterior wall and an interior wall, said exterior wall and said interior wall defining a vacuum sealed in-between space, said interior wall defining an interior cavity;
B) a top cap comprising first connecting end, a base and a first tab, said top cap being removably mounted to said upper end, said top cap being a twist off cap, said top cap further comprises a hypodermic device sup- porting portion, a retaining member and a supporting structure, wherein said base with said first connecting end mount upon said upper end, said first tab is fixedly mounted onto said base, said retaining member is disposed inside said supporting structure, and said supporting structure is adapted to rigidly support said retaining member, said hypodermic device supporting portion extends from said retaining member,
said retaining member has a bay having cooperative shape and dimensions to securely receive a hypodermic device supporting portion therein;
C) a bottom cap comprising second connecting end and a second tab, said bottom cap being removably mounted to said lower end, said bottom cap being a twist off cap; and
D) a hypodermic device having a proximal end and a distal end, said hypodermic device being housed inside said housing assembly, wherein said proximal end is aligned with said upper end and said distal end is aligned with said lower end, said proximal end being closed with said top cap and said distal end being closed with said bottom cap, said hypodermic device supporting portion has cooperative shape and dimen- sions to snugly hold said proximal end of said hypo- dermic device, said hypodermic device supporting por- tion comprises a wider portion, said wider portion extends beyond said first connecting end, said wider portion is accommodated inside said interior cavity and snugly fit onto said interior wall.

2. The housing for hypodermic device set forth in claim 1, wherein said hypodermic devices are auto injectors, epinephrine auto injectors, and insulin auto injectors.

3. The housing for hypodermic device set forth in claim 1, wherein said exterior wall and said interior wall are configured as vacuum sealed layers made of a rigid material that protect said hypodermic device from impact and acci- dental activation.

4. The housing for hypodermic device set forth in claim 3, wherein said rigid material is stainless steel or other material having similar characteristics.

5. The housing for hypodermic device set forth in claim 4, wherein said exterior wall and said interior wall are configured to keep said hypodermic device at a range of suitable temperature for a predetermined period of time, thus protecting said hypodermic device for securely storing and transportation, whereby said exterior wall comprises peripheral ridges.

6. The housing for hypodermic device set forth in claim 1, wherein said housing assembly has a substantially elliptical cross section with cooperative dimensions to receive said hypodermic device therein.

7. The housing for hypodermic device set forth in claim 1, wherein said top cap and said bottom cap are adapted to hold said hypodermic device centered inside said interior cavity.

8. The housing for hypodermic device set forth in claim 1, wherein said housing assembly further comprises a ring attachment adjacent to said upper end, said ring attachment is adapted to be used to secure said housing for hypodermic device to backpacks, purses, garments carried or worn.

9. A housing for hypodermic device, comprising: A) a housing assembly comprising an upper end, a lower end, an exterior wall and an interior wall, said exterior wall and said interior wall defining a vacuum sealed in-between space, said exterior wall comprises peripheral ridges, and said interior wall defining an interior cavity; B) a top cap comprising a first connecting end, a base and a first tab, said top cap being removably mounted to said upper end, said top cap being a twist off cap; C) a bottom cap comprising second connecting end and a second tab, said bottom cap being removably mounted to said lower end, said bottom cap being a twist off cap; and D) a hypodermic device having a proximal end and a distal end, said hypodermic device being housed inside said housing assembly, wherein said proximal end is aligned with said upper end and said distal end is aligned with said lower end, said proximal end being closed with said top cap and said distal end being closed with said bottom cap; wherein said top cap further comprises a hypodermic device supporting portion, a retaining member and a supporting structure, wherein said base with said first connecting ends mount upon said upper end, said first tab is fixedly mounted onto said base, said retaining member is disposed inside said supporting structure, and said supporting structure is adapted to rigidly support said retaining member, said hypodermic device supporting portion extends from said retaining member: wherein said retaining member has a bay having cooperative shape and dimensions to securely receive a hypodermic device supporting portion therein; wherein said hypodermic device supporting portion has cooperative shape and dimensions to snugly hold said proximal end of said hypodermic device, said hypodermic devi se supporting portion comprises a wider portion, said wider portion extends beyond said first connecting end, said wider portion is accommodated inside said interior cavity and snugly fit onto said interior wall.

10. The housing for hypodermic device set forth in claim 9, wherein said hypodermic devices are autoinjectors, epinephrine auto injectors, and insulin auto injectors.

11. The housing for hypodermic device set forth in claim 10, wherein said exterior wall and said interior wall are configured as vacuum sealed layers made of a rigid material that protect said hypodermic device from impact and accidental activation.

12. The housing for hypodermic device set forth in claim 11, wherein said rigid material is stainless steel or other material having similar characteristics.

13. The housing for hypodermic device set forth in claim 12, wherein said exterior wall and said interior wall are configured to keep said hypodermic device at a range of suitable temperature for a predetermined period of time, thus protecting said hypodermic device for securely storing and transportation.

14. The housing for hypodermic device set forth in claim 13, wherein said housing assembly has a substantially elliptical cross section with cooperative dimensions to receive said hypodermic device therein, wherein said top cap and said bottom cap are adapted to hold said hypodermic device centered inside said interior cavity, and wherein said housing assembly further comprises a ring attachment adjacent to said upper end, said ring attachment is adapted to be used to secure said housing for hypodermic device to backpacks, purses, garments carried or worn.

* * * * *